United States Patent [19]

Fish

[11] Patent Number: 5,389,338
[45] Date of Patent: Feb. 14, 1995

[54] APPARATUS FOR DRY CHEMICAL ANALYSIS OF FLUIDS

[75] Inventor: Falk Fish, Tel Aviv, Israel

[73] Assignee: Orgenics Ltd., Yavne, Israel

[21] Appl. No.: 101,965

[22] Filed: Aug. 4, 1993

Related U.S. Application Data

[63] Continuation-in-part of Ser. No. 816,280, Jan. 3, 1992, abandoned.

Foreign Application Priority Data

Jan. 6, 1991 [IL] Israel ............ 96887

[51] Int. Cl.⁶ .......... G01N 33/00; G01N 21/00
[52] U.S. Cl. .......... 422/58; 422/56; 436/86
[58] Field of Search .......... 422/56–58; 436/1, 86

[56] References Cited

U.S. PATENT DOCUMENTS

| | | | |
|---|---|---|---|
| 2,785,057 | 3/1957 | Schwab | 23/253 |
| 3,507,269 | 4/1970 | Berry | 23/253 |
| 3,539,300 | 11/1970 | Stone | 23/253 |
| 3,798,004 | 3/1974 | Zerachia | 23/253 |
| 3,802,842 | 4/1974 | Lange et al. | 436/86 |
| 3,811,840 | 5/1974 | Bauer | 435/7 |
| 3,968,010 | 7/1976 | Young | 195/103 SR |
| 3,996,006 | 12/1976 | Nagano | 23/253 |
| 4,046,514 | 9/1977 | Johnston | 23/256 |
| 4,059,407 | 11/1977 | Hochstrasser | 23/253 |
| 4,189,304 | 2/1980 | Adams | 422/56 |
| 4,246,339 | 1/1981 | Cole | 433/7 |
| 4,256,693 | 3/1981 | Kondo | 422/76 |
| 4,541,987 | 9/1985 | Guadagno | 422/56 |
| 4,559,949 | 12/1985 | Levine | 422/58 |
| 4,562,045 | 12/1985 | Murata | 422/56 |
| 4,647,430 | 3/1987 | Zweig | 422/56 |
| 4,668,472 | 5/1987 | Sakamoto | 422/56 |
| 4,678,757 | 7/1987 | Rapkin | 422/56 |
| 4,738,823 | 4/1988 | Engelmann | 422/56 |
| 4,774,054 | 9/1988 | Charlton | 422/56 |
| 4,787,629 | 11/1988 | DeMeyer | 272/123 |
| 4,804,518 | 2/1989 | Levine | 422/56 |
| 4,818,671 | 4/1989 | Hay-Kaufmann | 422/56 |
| 4,850,610 | 8/1989 | Maggio | 422/58 |
| 4,859,340 | 8/1989 | Hoy | 210/502.1 |
| 4,895,808 | 1/1990 | Romer | 436/178 |
| 4,912,034 | 3/1990 | Kaha et al. | 435/7.92 |
| 4,916,056 | 4/1990 | Brown | 435/7 |
| 4,939,096 | 7/1990 | Tonelli | 422/58 |
| 4,939,097 | 7/1990 | Lawrence | 422/56 |
| 4,956,300 | 9/1990 | Wells | 436/66 |
| 4,959,196 | 9/1990 | Moisson | 422/56 |
| 4,962,043 | 10/1990 | Nagase | 422/57 |
| 4,971,914 | 11/1990 | Lawrence | 436/66 |

FOREIGN PATENT DOCUMENTS 0269876 6/1988 European Pat. Off.
0336483 10/1989 European Pat. Off.

Primary Examiner—Lyle A. Alexander
Attorney, Agent, or Firm—Ladas & Parry

[57] ABSTRACT

Apparatus for dry chemical analysis of fluids comprising a filter, a filter holder apparatus including a base member defining a filter supporting location and a filter retaining apparatus including a mesh arranged to retain the filter at the filter supporting location in spaced relationship with respect to the mesh.

16 Claims, 3 Drawing Sheets

5,389,338

APPARATUS FOR DRY CHEMICAL ANALYSIS OF FLUIDS

This is a continuation of application Ser. No. 07/816,280, filed on Jan. 3, 1992, now abandoned.

FIELD OF THE INVENTION

The invention relates to apparatus for dry chemical analysis of fluids.

BACKGROUND OF THE INVENTION

Test devices for dry chemical analysis of fluids typically include one or more reagent matrix areas retained in a holder or attached to a substrate. These reagent matrix areas detect chemical components of sample liquids by a color reaction formed when the reagent contacts the liquid sample.

Test devices or strips for dry chemical analysis of fluids are well established in the art and used in agriculture, industry and medicine. For these applications it is desirable that the test devices be simple and inexpensive to produce.

Such devices are described in U.S. Pat. Nos. 4,774,054, 3,798,004 and 4,647,430 in which multilayer filters are glued to a substrate. The use of glue, however, can have a detrimental effect on the reagents used and their storage life as well as complicating the assembly of the device.

The use of a filter holder in a test device, such as in U.S. Pat. No. 4,912,034, eliminates the need for the use of glue in the test device, but also increases the device's complexity.

A simplified filter holder test device is described in U.S. Pat. No. 2,785,057, however this device employs a perforated disk filter retaining member abutting an absorbent layer which would not be suitable for chemical analysis of whole blood samples.

Accordingly there is a need in the art for a simple device for dry chemical analysis of fluids which can be used for chemical analysis of whole blood samples. The present invention fulfills this need and provides related advantages.

SUMMARY OF THE INVENTION

There is thus provided in accordance with the present invention apparatus for dry chemical analysis of fluids comprising a filter, a filter holder apparatus including a base member defining a filter supporting location and a filter retaining apparatus including a mesh arranged to retain the filter at the filter supporting location in spaced relationship with respect to the mesh.

In accordance with a preferred embodiment of the invention the base member is generally rigid.

In accordance with another preferred embodiment of the invention the filter supporting location includes a depression.

In accordance with yet another preferred embodiment of the invention the base member is elongated and comprises first and second ends and wherein the depression in the base member is located at the first end.

In accordance with still another preferred embodiment of the invention the filter retaining apparatus abuts the base member and the base member and the filter retaining apparatus are mechanically joined.

In accordance with a further preferred embodiment of the invention the filter retaining apparatus has an outer side surface and the base member has an inner side surface which encloses the side surface of the filter retaining apparatus.

In accordance with yet a further preferred embodiment of the invention a portion of the side surface of the filter retaining apparatus is formed with flange and a portion of the side surface of the base member is formed with a notch and wherein the flange engages the notch to mechanically join the filter retaining apparatus to the base member.

In accordance with still a further preferred embodiment of the invention the filter retaining apparatus additionally includes an outer solid portion surrounding the mesh.

In accordance with a preferred embodiment of the invention the filter retaining apparatus additionally includes protuberances depending perpendicularly from the mesh and wherein the protuberances abut the filter for retaining the filter within the depression and for providing even distribution of a sample liquid on a surface of the filter.

In accordance with another preferred embodiment of the invention the filter retaining apparatus additionally includes protuberances depending perpendicularly from a part of the solid portion adjacent the mesh and wherein the protuberances abut the filter for retaining the filter within the depression.

In accordance with still another preferred embodiment of the invention the filter retaining apparatus additionally includes a flange depending perpendicularly from the solid portion adjacent the mesh and wherein the flange is spaced from the filter for increasing the rate of flow of sample liquid to the filter and for reducing the seepage of sample liquid from the depression along an interface between the base member and the solid portion of the filter retaining apparatus.

In accordance with yet another preferred embodiment of the invention the filter holder apparatus is fabricated from a hydrophilic material.

In accordance with a further preferred embodiment of the invention at least one surface of the base member is treated to induce hydrophilousity.

In accordance with a still further preferred embodiment of the invention at least one surface of the filter retaining apparatus is treated to induce hydrophilousity.

In accordance with yet a further preferred embodiment of the invention the filter retaining apparatus is formed from an injection moldable plastic.

In accordance with another preferred embodiment of the invention the base member is formed from an injection moldable plastic.

In accordance with still another preferred embodiment of the invention the filter holder apparatus does not exceed 5 cm in length, 2 cm in width and 0.5 cm in depth.

In accordance with yet another preferred embodiment of the invention the base member includes an aperture disposed between the depression and a bottom surface of the base member to permit fluid communication between the depression and the bottom surface of the base member.

In accordance with a further preferred embodiment of the invention the filter is a multilayer filter.

In accordance with a still further preferred embodiment of the invention one layer of the multilayer filter includes a reagent impregnated material. In accordance with another preferred embodiment of the invention a portion of the filter retaining means abuts said base member and said base member and said filter retaining means are engaged by press fit means.

BRIEF DESCRIPTION OF THE DRAWINGS

The present invention will be understood and appreciated more fully from the following detailed description taken in conjunction with the drawings in which.

DETAILED DESCRIPTION OF PREFERRED EMBODIMENTS

Figure 1A:
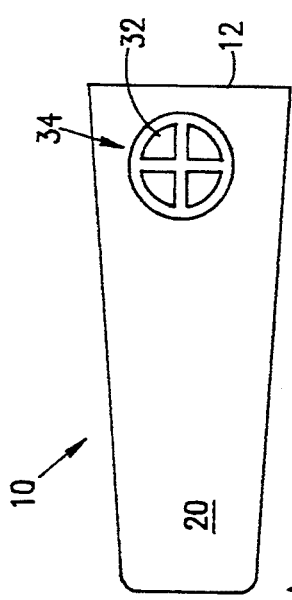
FIG. 1A is a schematic top view illustration of apparatus for dry chemical analysis of fluids constructed and operative in accordance with a preferred embodiment of the invention.
Figure 1B:
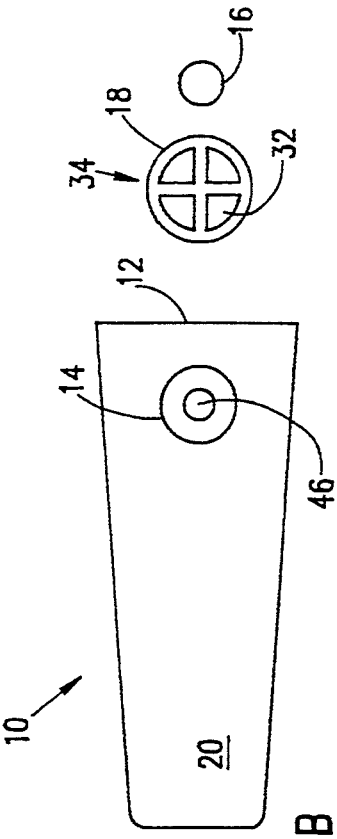
FIG. 1B is a schematic view illustration of the unassembled apparatus of FIG. 1A.
Figure 1C:
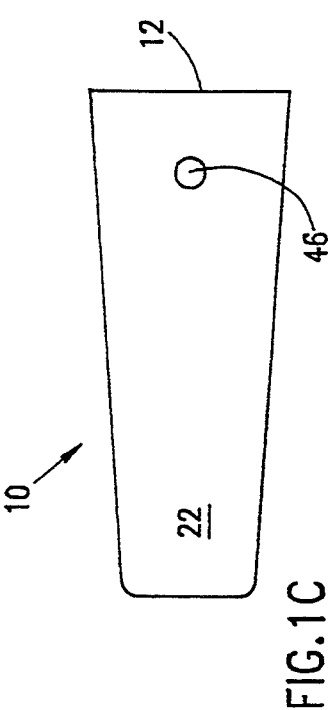
FIG. 1C is a schematic bottom view of the apparatus of FIG. 1A.
Figure 2A:
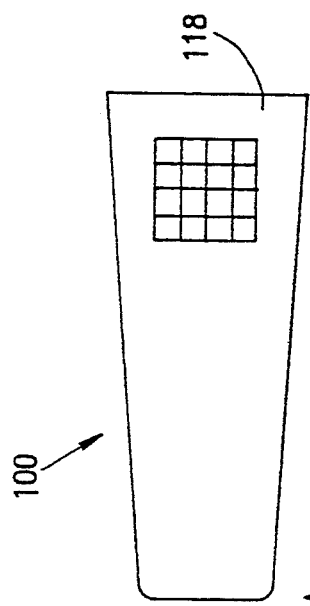
FIG. 2A is a schematic top view illustration of a filter retaining apparatus in an alternative embodiment of the apparatus of FIG. 1A.
Figure 2B:
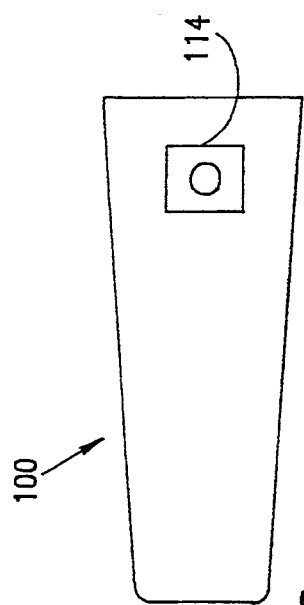
FIG. 2B is a schematic top view of the top surface of the base member in an alternative embodiment of the apparatus of FIG. 1B.
Figure 2C:
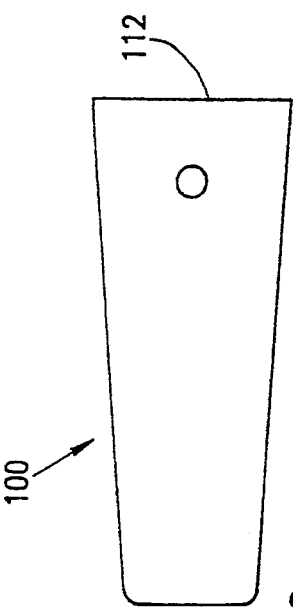
FIG. 2C is a schematic bottom view illustration of the bottom surface of the base member in an alternative embodiment of the apparatus of FIG. 1C.
Figure 3:
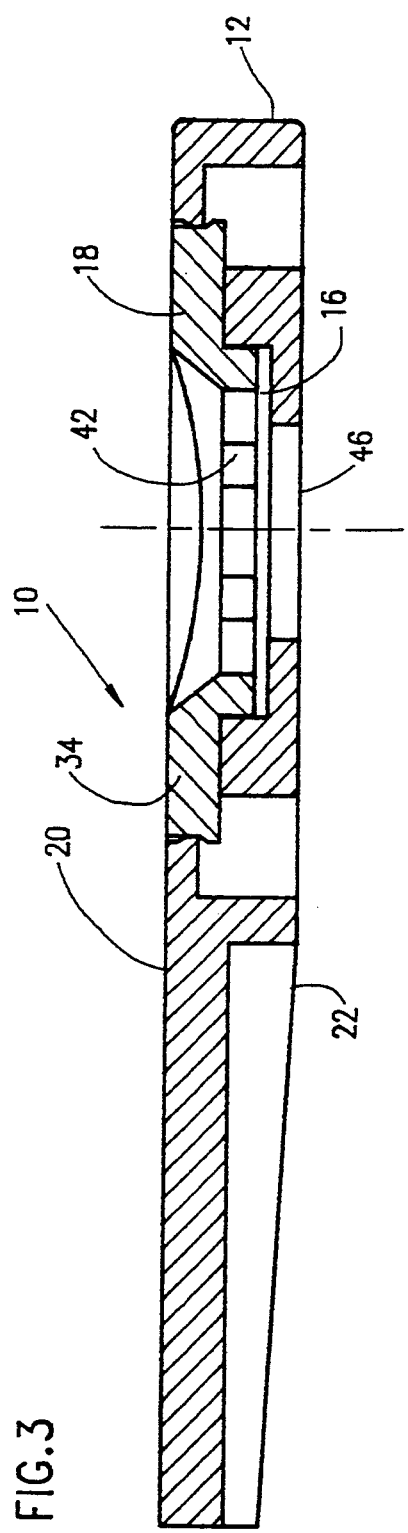
FIG. 3 is a schematic side sectional view illustration of the apparatus of FIG. 1.
Figure 5:
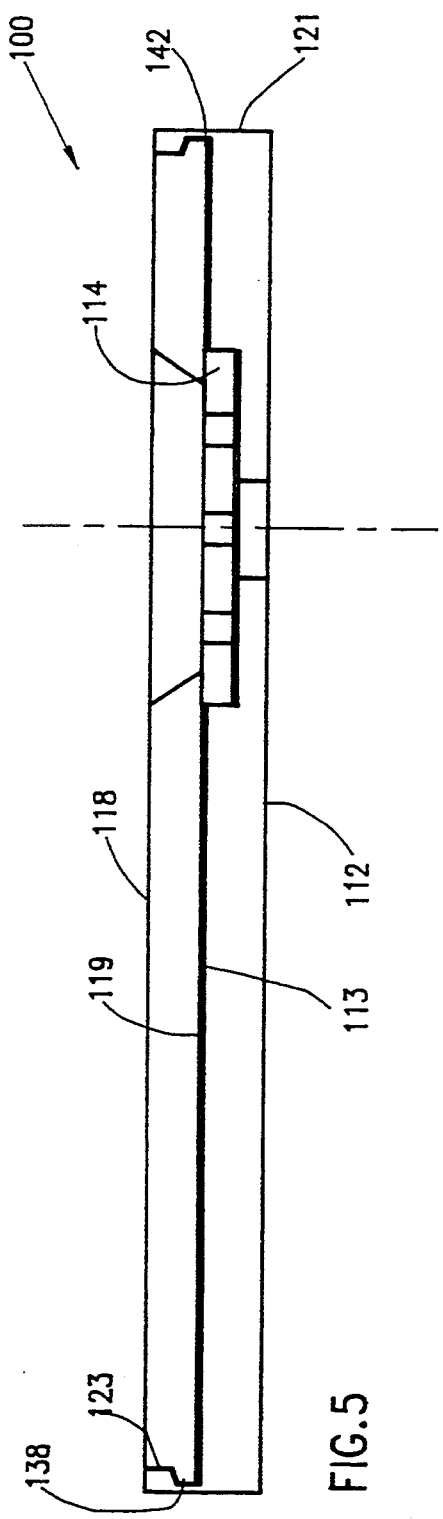
FIG. 5 is a schematic side sectional view of the apparatus of FIG. 2.

Reference is now made to FIGS. 1A, 1B, 1C, 3 and 4A which illustrate apparatus for dry chemical analysis of fluids constructed and operative in accordance with a preferred embodiment of the present invention and comprising a generally elongated shaped filter holder 10 having a base member 12 approximately 5 cm long, 2 cm wide and 0.5 cm thick with a top surface 20 and a bottom surface 22.

One end of the base member 12 has a typically circular depression 14 extending from top surface 20 toward bottom surface 22. The diameter of depression 14 is approximately 1.2 cm at the level of top surface of 20. At a depth of 0.10 cm depression 14 sharply narrows to a diameter of 0.70 cm forming a ledge 24. Ledge 24 separates upper portion 25 of depression 14 from a lower portion 26. At the level of ledge 24 depression 14 has a wall in which a notch 40 is formed. Lower portion 26 has a base 44 which is approximately 0.20 cm from top surface 20 and 0.1 cm from ledge 24 and from which a bore 46 extends to the bottom surface 22 of base member 12.

Filter 16 is disposed in the lower portion 26 of depression 14. Filter 16 is typically 0.1 mm–1.0 mm thick and has approximately the same diameter as the lower portion 26 of depression 14.

Filter 16 is retained in depression 14 by filter retaining apparatus 18. Filter retaining apparatus 18 has a solid portion 34 surrounding an irregular mesh surface portion 32. Irregular mesh surface portion 32 has an average mesh opening of approximately 2–4 mm.

Filter retaining apparatus 18 additionally has an upper portion 28 and a lower portion 30. The solid portion 34 of filter retaining apparatus 18 has a side surface from which a flange 38 laterally extends. The lower portion 30 of filter retaining apparatus 18 includes protuberances 42 depending perpendicularly from the mesh surface portion 32 and from a part of the solid portion 34 of filter retaining apparatus 18.

Lower portion 30 of filter retaining apparatus 18 is sized to fit tightly into lower portion 26 of depression 14 with the protuberances 42 abutting filter 16. Upper portion 28 of filter retaining apparatus 18 is sized to fit tightly into upper portion 25 of depression 14. The solid portion 34 of filter retaining apparatus 18 rests on ledge 24 and flange 38 engages notch 40 to mechanically join filter retaining apparatus 18 to base member 12. Filter 16 is thus securely retained in depression 14.

Filter 16 is typically a multilayer filter in which the top layer is a glass fiber filter and the bottom layer is a reagent impregnated nylon membrane.

Filter retaining apparatus 18 and base member 12 are typically fabricated from a plastic material which although generally rigid is flexible enough to permit flange 38 to flex during assembly of apparatus 10. During assembly of apparatus 10 filter 16 is first placed in depression 14. Retaining apparatus 18 is then inserted in depression 14 and gently pressed toward bottom surface 22 of base member 12. Flange 38 is deformed until solid portion 34 abuts ledge 24 releasing the pressure on flange 38. Flange 38 then returns to its original shape and engages notch 40.

Filter retaining apparatus 18 and base member 12 are typically fabricated by injection molding from ABS plastic. Other plastics, however, such as polystyrene or polypropylene may alternatively be used as well as other fabrication methods such as blow molding.

Typically, filter retaining apparatus 18 and base member 12 are treated to make their surfaces hydrophilic. This treatment typically includes first exposing filter retaining apparatus 18 and base member 12 to a corona discharge for approximately 1–5 seconds at a distance of 1 mm from the electrode. For the filter retaining apparatus 18 the treatment additionally typically includes a brief complete immersion in a surfactant solution such as a 0.01–0.5M solution of dioctyl sulfosuccinate sodium salt dissolved in a 4:6 alcohol water mixture. Alternatively, filter retaining apparatus 18 and base member 12 may be fabricated from a hydrophilic material.

In using the apparatus 10 illustrated in FIGS. 1A, 1B, 1C, 3 and 4 a sample liquid, typically whole blood, is placed on mesh surface portion 32 of filter retaining apparatus 18. The blood is generally evenly distributed in the space over the glass fiber filter layer by the mesh surface portion 32 and the protuberances 42.

The blood is then drawn through the glass fiber filter by gravity and capillary action. The glass fiber filter separates the formed portion of the blood, such as erythrocytes, from the liquid portion which is passed on to the reagent impregnated nylon membrane.

When the liquid portion of the blood contacts the nylon membrane, chemical components of the blood react with reagents in the nylon membrane to cause a color change in the reagents thus detecting the presence and/or concentration of these chemical components. This color change can be seen from the bottom surface 22 of base member 12 through a bore 46. Bore 46 also permits excess liquid to pass out of the lower portion of base member 12 to prevent backflow pressure, which would interfere with the flow of the sample liquid through the filter.

Reference is now made to FIGS. 2A, 2B, 2C and 5 which illustrate an alternative preferred embodiment of the present invention. This embodiment of apparatus for dry chemical analysis of fluids (labeled 100 in the figures) differs from the embodiment of FIGS. 1A, 1B, 1C, 3 and 4A only in that filter retaining apparatus 118 and base member 112 have respective bottom surfaces 119 and top surfaces 113 which are congruent at all points except depression 114. Retaining member 118 and base member 112 are joined mechanically in apparatus similar to that illustrated in the embodiment of FIGS. 1A, 1B, 1C, 3 and 5. Base member 112 has a perimeter surface 121 formed with a notch 142. Retaining member 118 has a perimeter surface 123 formed with a flange 138. When bottom surface 119 of filter retaining apparatus 118 abuts top surface 113 of base member 112, flange 138 engages notch 142 mechanically joining filter retaining apparatus 118 to base member 112.

Figure 4A:
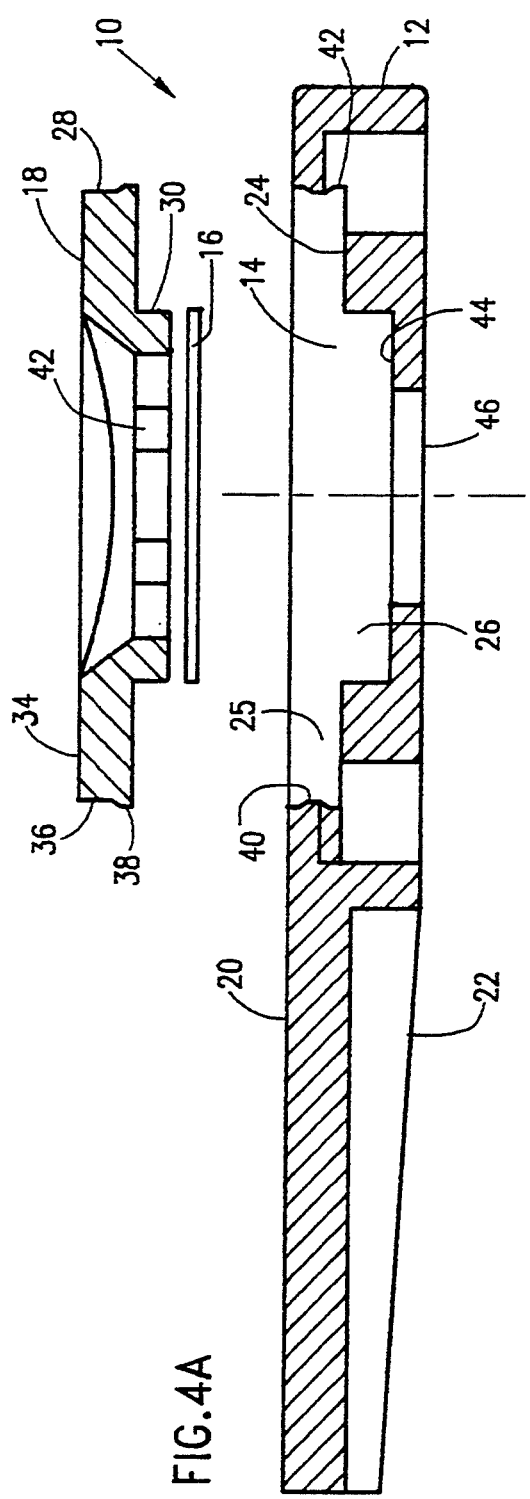
FIG. 4A is an exploded schematic side sectional view illustration of the apparatus of FIG. 1.
Figure 4B:
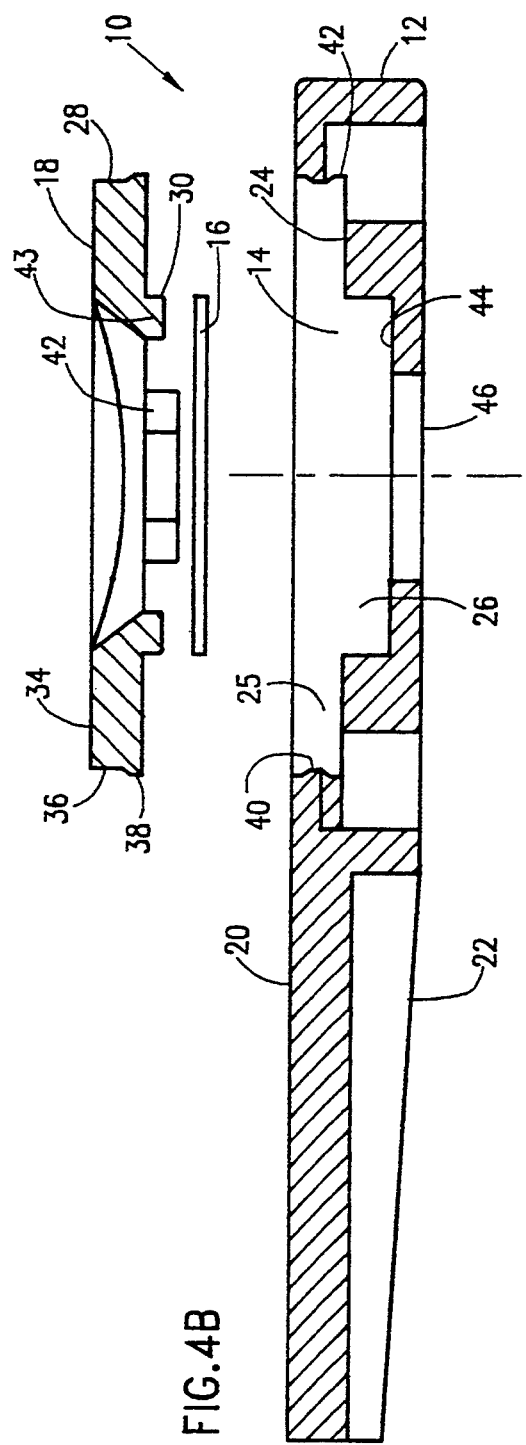
FIG. 4B is an exploded schematic side sectional view of an alternative embodiment of the apparatus of FIG. 4A.

Reference is now made to FIG. 4B which illustrates an alternative embodiment of the invention in which a flange 43 depends perpendicularly from the solid portion of the filter retaining apparatus 18 and is spaced from filter 16. Flange 43 which is adjacent to and surrounding the mesh surface portion 32 is spaced from the filter 16 to increase the rate of flow of sample liquid to filter 16 and to reduce seepage of the sample liquid from depression 14 along the interface between base member 12 and the solid portion 34 of filter retaining apparatus 18.

It will be appreciated by persons skilled in the art that the present invention is not limited to what has particularly been shown and described hereinabove. It is therefore intended that the scope of the invention be defined only by the claims which follow.

I claim:

1. Apparatus for dry chemical analysis of fluids containing color particulate suspension such as whole blood, comprising:
   a rigid base member defining an aperture and a filter supporting location above said aperture, wherein said filter supporting location includes a depression;
   a filter including a reagent capable of colorimetric changes in the presence of an analyte; and
   rigid filter retaining means including a rigid mesh, engaging said filter and said base member to retain said filter non-adhesively on said filter supporting location between said rigid mesh and said aperture, said filter retaining means further including protuberances depending perpendicularly from said mesh, wherein said protuberances abut said filter for retaining said filter within said depression in spaced relationship with respect of said mesh, and for providing even distribution of a sample liquid on a surface of said filter.

2. Apparatus according to claim 1 wherein said base member is elongated and comprises first and second ends and wherein said depression in said base member is located at said first end.

3. Apparatus according to claim 1 wherein a portion of said filter retaining means abuts said base member and said base member and said filter retaining means are engaged by press fit means.

4. Apparatus according to claim 1 wherein said filter retaining means has an outer side surface and said base member has an inner side surface which encloses said outer side surface of said filter retaining means.

5. Apparatus according to claim 1 wherein said base member and said filter retaining means are fabricated from a hydrophilic plastic material.

6. Apparatus according to claim 1 wherein said base member is fabricated from plastic and has at least one surface which has hydrophilic properties.

7. Apparatus according to claim 1 wherein said filter retaining means is fabricated from plastic and has at least one surface which has hydrophilic properties.

8. Apparatus according to claim 1 wherein said filter retaining means is formed from an injection moldable plastic.

9. Apparatus according to claim 1 wherein said base member is formed from an injection moldable plastic.

10. Apparatus according to claim 1 wherein said filter holder means does not exceed 5 cm in length, 2 cm in width and 0.5 cm in depth.

11. Apparatus according to claim 1 wherein said mesh has an average mesh opening of 2–4 mm.

12. Apparatus according to claim 1 wherein said filter is a multilayer filter.

13. Apparatus according to claim 12 wherein one layer of said multilayer filter includes a reagent impregnated material.

14. Apparatus according to claim 1 wherein said filter retaining means additionally includes an outer solid portion surrounding said mesh.

15. Apparatus according to claim 14 wherein said filter retaining means additionally includes protuberances depending perpendicularly from a part of said solid portion adjacent said mesh and wherein said protuberances abut said filter for retaining said filter within said depression.

16. Apparatus according to claim 14 wherein said filter retaining means additionally includes a flange depending perpendicularly from said solid portion adjacent said mesh and wherein said flange is spaced from said filter for increasing the rate of flow of the sample liquid to said filter and for reducing seepage of the sample liquid from said depression along an interface between said base member and said solid portion of said filter retaining means.

* * * * *